United States Patent
Turner (10) Patent No.: US 10,835,661 B2
(45) Date of Patent: Nov. 17, 2020

(54) BLOOD ANALYSIS APPARATUS AND METHOD

(71) Applicant: Spectrum Medical Ltd, Gloucester, Gloucestershire (GB)

(72) Inventor: Stephen Turner, Gloucester (GB)

(73) Assignee: Spectrum Medical Ltd., Gloucester (GB)

( * ) Notice: Subject to any disclaimer, the term of this patent is extended or adjusted under 35 U.S.C. 154(b) by 571 days.

(21) Appl. No.: 15/555,765

(22) PCT Filed: Mar. 3, 2016

(86) PCT No.: PCT/GB2016/050554
§ 371 (c)(1),
(2) Date: Sep. 5, 2017

(87) PCT Pub. No.: WO2016/142657
PCT Pub. Date: Sep. 15, 2016

(65) Prior Publication Data
US 2018/0050146 A1    Feb. 22, 2018

(30) Foreign Application Priority Data
Mar. 6, 2015    (GB) .................................. 1503805.2

(51) Int. Cl.
*A61M 1/16* (2006.01)
*A61M 1/36* (2006.01)

(52) U.S. Cl.
CPC ........ *A61M 1/1698* (2013.01); *A61M 1/3609* (2014.02); *A61M 1/3666* (2013.01);
(Continued)

(58) Field of Classification Search
CPC .............. A61M 1/1698; A61M 1/3609; A61M 1/3666; A61M 1/3667; A61M 2205/205;
(Continued)

(56) References Cited

U.S. PATENT DOCUMENTS 5,865,784 A    2/1999   Faithfull et al.
2003/0215356 A1   11/2003  Patterson et al.
(Continued)

FOREIGN PATENT DOCUMENTS

CN    1192155    9/1998
GB    2 485 558   5/2012
(Continued)

OTHER PUBLICATIONS

United Kingdom Intellectual Property Office, Search Report under Section 17, Application No. GB1503805.2, dated Nov. 30, 2015, 4 pages.
(Continued)

*Primary Examiner* — Benjamin J Klein
(74) *Attorney, Agent, or Firm* — Sunstein LLP (57) ABSTRACT

A blood gas analysis method (100) is provided for determining the partial pressure of oxygen of arterial blood exiting an oxygenator, wherein the oxygenator generates arterial blood by exposing venous blood to an oxygenation gas and releases excess oxygenation gas as exhaust gas. The method (100) comprises a step (140) of determining an estimate of the partial pressure of oxygen in the exhaust gas, a step (150) of determining the blood oxygen uptake in the oxygenator, and a step (160) of determining the partial pressure of oxygen in the arterial blood by adjusting the estimate using the blood oxygen uptake value. Used in a clinical setting, the method (100) allows a more accurate output of the partial pressure of oxygen in the arterial blood to be provided, which facilitates oxygenator operation.

18 Claims, 4 Drawing Sheets

(52) U.S. Cl.
CPC ... *A61M 1/3667* (2014.02); *A61M 2205/3331* (2013.01); *A61M 2205/3334* (2013.01); *A61M 2205/3368* (2013.01); *A61M 2230/205* (2013.01)

(58) Field of Classification Search
CPC .............. A61M 1/3334; A61M 1/3368; G01N 33/4925
See application file for complete search history.

(56) References Cited

U.S. PATENT DOCUMENTS

2006/0015056 A1    1/2006  Ellingboe et al.
2009/0210162 A1*  8/2009  Kristiansen ......... A61M 1/1698
702/19

FOREIGN PATENT DOCUMENTS

| | | |
|---|---|---|
| JP | S6316265 | 1/1988 |
| WO | WO 2007/075089 | 7/2007 |
| WO | WO 2012/066280 | 5/2012 |

OTHER PUBLICATIONS

J. Martin Amezaga Authorized officer European Patent Office, International Search Report—Application No. PCT/GB2016/050554, dated May 27, 2016, 14 pages, together with the Written Opinion of the International Searching Authority.

* cited by examiner

BLOOD ANALYSIS APPARATUS AND METHOD

FIELD OF THE INVENTION

The present invention relates to blood gas analysis. More specifically, the present invention relates to apparatus and methods for determining values indicative of blood oxygenation. In particular, the present invention relates to the determination of the partial pressure of oxygen in blood.

BACKGROUND OF THE INVENTION

Certain medical procedures require the heart or lung of a patient to be kept still. This may be necessary in order for a surgeon to perform surgical procedures, such as cardiac surgery. While the heart is unable to circulate blood or the lung is unable to re-oxygenate blood or to remove carbon dioxide, heart-lung machines are used for life support, providing extracorporeal oxygenation to maintain a supply of oxygen to a patient.

More recently, extracorporeal oxygenation has been explored for the management of viral infections (such as H1N1) that affect lung function by causing pulmonary embolisms. Patients suffering from such infections may require long-term ventilation, in the region of several weeks (typically 20 days, but in severe cases ventilation may be required for several months, e.g. for up to 180 days), in order to facilitate treatment and drainage of the lung, and in order to permit the lung to rest and heal while the patient's immune system is given an opportunity to defeat the viral infection.

The partial pressures of oxygen and carbon dioxide, pO2 and pCO2, are indicative of physiological activity and, thus, of interest for extracorporeal oxygenation management. PCT-published application WO2012066280 by the present applicant discloses a method and apparatus for determining pO2 and/or pCO2 as a function of, inter alia, the amount of carbon dioxide CO2 entering and exiting a ventilation machine.

The present invention seeks to increase the repertoire of options for monitoring the partial pressures of blood gases.

SUMMARY OF THE INVENTION

In accordance with a first aspect of the invention, there is disclosed a blood gas analysis method for determining the partial pressure of oxygen of arterial blood as defined by claim 1.

The method is suitable for an oxygenator of the type configured to generate arterial blood by exposing venous blood to oxygen from an oxygenation gas and to allow passage of excess oxygenation gas as exhaust gas.

The method comprises the steps of: determining one or more gas values, the gas values comprising an estimate of the partial pressure of oxygen in the exhaust gas, determining one or more blood values, the blood values comprising a blood oxygen uptake value indicative of an amount of oxygen taken up by the blood in the oxygenator, and generating an output of the partial pressure of oxygen in the arterial blood by adjusting the estimate using the blood oxygen uptake value.

Many existing methods for determining the partial oxygen pressure of blood require a sensor in physical contact with the blood. An example of an existing pO2 sensor is the well-known Clark electrode, which requires physical contact with the sample (e.g., blood) to enable oxygen molecules to interact with an electrode surface.

A contact measurement is used as oxygen dissolved in blood does not exhibit a good contrast for non-contact sensors, because blood does not change colour or absorption characteristics depending on the concentration of oxygen dissolved in blood plasma.

This differs from oxygen bound to haemoglobin, which provides optical contrast as the redness of blood changes.

Some commercially available systems use optical sensors to determine the partial pressure of oxygen in blood, but these require an external contrast agent to be injected capable of providing contrast dependent on oxygen bound to the contrast agent.

The present applicant has appreciated that a good estimate of the partial pressure of oxygen in arterial blood can be obtained by first determining an initial estimate of the partial pressure of oxygen in the exhaust gas, and by adjusting the initial estimate based on the oxygen uptake by the blood passing the oxygenator. The blood oxygen uptake can be determined with optical sensors. Herein, optical sensors are regarded as non-contact sensors because the optical radiation does not require physical contact with blood.

This allows the partial pressure of oxygen in blood to be determined without requiring a sensor coming into contact (such as the Clark electrode) and without an external contrast agent to be injected into the blood.

The influence of the blood uptake becomes more pronounced at low oxygenation rates, e.g., when oxygenation gas with a low oxygen content is used, or when oxygenation gas is supplied at a low flow rate. Thus, the effect of improving the accuracy of an output achieved by accounting for the blood oxygen uptake is stronger the lower the oxygenation rate. However, in a clinical setting it is impractical having to define a strict cut-off as to what constitutes a "low" oxygenation rate. The present method may be used independently of the oxygenation rate, thus helping to facilitate oxygenator operation.

Operation of an oxygenator may be facilitated by providing an output to an operator, such a member of the surgical team, for them to decide on the course of the extracorporeal ventilation. The output may be generated, and provided, continuously as a real time measurement, as will be set out in more detail below. The operation may be facilitated by automating oxygenation management. For instance, the output of the partial pressure of oxygen in the arterial blood may be used to control oxygenation parameters. The output may be used to implement a closed loop control of oxygenation parameters.

Embodiments of the first aspect are defined in the claims dependent on claim 1.

In embodiments of the first aspect, the blood oxygen uptake value is derived by determining an arterial oxygen saturation of the arterial blood, determining a venous oxygen saturation of the venous blood, and calculating the blood oxygen uptake value as a function of the difference between the arterial oxygen saturation and the venous oxygen saturation.

The oxygen saturation may be measured by optical sensors. Sensor systems exist that allow the oxygen saturation of the venous blood (entering an oxygenator) and of arterial blood (leaving the oxygenator) to be measured through a blood line. This allows the pre- and post-oxygenation oxygen saturation to be measured with a non-contact sensor. Furthermore, such sensors may be fitted to existing equipment, avoiding a need to replace existing blood lines.

Using both the arterial oxygen saturation and the venous saturation as a basis to calculate partial oxygen pressure was hitherto not explored because it was believed that these values do not provide sufficient accuracy.

In embodiments of the first aspect, the blood oxygen uptake value and/or the output of the partial pressure of oxygen in the arterial blood is calculated as a function dependent on one or more of: the flow rate, the temperature, and/or the haemoglobin concentration of the blood passing through the oxygenator.

The oxygenation efficiency of different types of oxygenators may differ. Thus, a higher degree of accuracy can be achieved by taking into account influences of the flow rate, temperature, or haemoglobin concentration of the blood passing through the oxygenator.

In embodiments of the first aspect, determining the estimate of the partial pressure of oxygen in the exhaust gas comprises obtaining a measurement of the partial pressure of oxygen in the exhaust gas and using the measurement as the estimate.

The applicant of the present invention has explored several options for obtaining an initial estimate of the partial oxygen pressure. Surprisingly, a direct measurement of the exhaust gas at the oxygenator provides a suitably accurate initial estimate. Such a measurement may be taken at any suitable location, e.g., at the exhaust port of an oxygenator.

In embodiments of the first aspect, determining the estimate of the partial pressure of oxygen in the exhaust gas comprises the steps of: determining a plurality of gas values, wherein the gas values comprise the amount of oxygen in the exhaust gas and the amount of exhaust gas leaving the oxygenator, determining the fraction of oxygen in the exhaust gas as a quotient of the amount of oxygen in the exhaust gas and the amount of exhaust gas, and deriving the estimate of the partial pressure of oxygen in the exhaust gas from the fraction of oxygen in the exhaust gas.

Another option for obtaining an initial estimate of the partial oxygen pressure is to determine the amount of oxygen in the exhaust gas relative to the total exhaust gas. The amount of oxygen in the exhaust gas may be estimated indirectly, as set out below.

In embodiments of the first aspect, determining the amount of oxygen in the exhaust gas comprises the steps of: determining an inlet gas value indicative of the amount of oxygen entering the oxygenator, determining the blood oxygen uptake value as a function of the flow rate and the haemoglobin concentration of the blood passing through the oxygenator, and determining the amount of oxygen in the exhaust gas based on the difference between the inlet gas value and the blood oxygen uptake value.

This provides a route to determining the amount of oxygen in the exhaust gas indirectly, i.e., without requiring a direct measurement at the oxygenator exhaust port. For reasons set forth below, the amount of gas passing through the oxygenator exhaust port may not be indicative of the amount of gas leaving the gas-blood interface in the oxygenator. Thus, determining the amount of oxygen in the exhaust gas indirectly provides a route to a more accurate estimate of the partial pressure of oxygen.

In embodiments of the first aspect, determining the amount of exhaust gas leaving the oxygenator comprises using a flow-control oxygenation system to set the flow rate of the exhaust gas and to derive the amount of exhaust gas from the flow rate parameters as controlled by the flow-control oxygenation system.

The total amount of gas passing the oxygenator exhaust port may not necessarily correspond to the amount of exhaust gas leaving the gas-blood interface inside the oxygenator. Determining the total amount of exhaust gas indirectly provides a route to a more accurate estimate of the partial pressure of oxygen.

In embodiments of the first aspect, the amount of exhaust gas leaving the oxygenator is calculated as a function of one or more gas values, the gas values comprising one or more of the total amount of the oxygenation gas, the amount or fraction of oxygen in the oxygenation gas, the amount or fraction of carbon dioxide in the oxygenation gas, and the amount or fraction of carbon dioxide in the exhaust gas.

In embodiments of the first aspect, the amount of exhaust gas leaving the oxygenator is calculated as a function of one or more blood values, the blood values comprising one or more of the flow rate, the temperature, the pressure, the haemoglobin concentration, or the oxygen saturation, of the blood entering and/or exiting the oxygenator.

The total amount of gas passing the oxygenator exhaust port may be calculated as a function of the gas entering the oxygenator and the gas taken up and released by the blood in the oxygenator. This provides another route to a more accurate estimate of the partial pressure of oxygen by determining the total amount of exhaust gas indirectly.

In accordance with a second aspect of the invention, there is provided a method of characterising the oxygenation efficiency of an oxygenator as defined by claim 11.

The method in accordance with the second aspect comprises the steps of the first aspect, and the steps of: providing one or more blood samples and oxygenating each blood sample in the oxygenator, determining the blood values for each sample, determining the gas values for each sample, determining for each sample as a sample-specific output the output of the partial pressure of oxygen in the arterial blood, determining for each sample a sample-specific reference value of the partial pressure of oxygen in the arterial blood, calculating, for each sample, an offset value indicating any difference between the sample-specific output and the sample-specific reference value, and generating one or more coefficients based on one or more offset values to describe the oxygenation efficiency of the oxygenator.

Embodiments of the second aspect are defined in the claims dependent on claim 10.

The one or more coefficients may be part of a mathematical model for describing the oxygenation efficiency of the oxygenator.

The accuracy of the output of the partial pressure of oxygen in the blood may be increased by taking into account the performance of a given oxygenator type or operation conditions. The applicant of the present invention has appreciated that the blood oxygenation performance, or oxygenation efficiency, of oxygenator models can be characterised by coefficients which can be determined in advance. This also provides the opportunity to store coefficients for multiple oxygenator models for later use.

In embodiments of the second aspect, each blood sample is oxygenated under different oxygenation conditions, the oxygenation conditions comprising one or more of a blood flow rate through the oxygenator, blood temperature, pressure, haemoglobin concentration, inlet gas flow rate, inlet gas oxygen fraction, inlet gas carbon dioxide fraction, oxygen saturation of the blood entering the oxygenator, or combinations thereof.

In embodiments of the second aspect, the coefficients are generated as a function of one or more of the different oxygenation conditions and/or as a function of the oxygen saturation of the blood sample leaving the oxygenator.

In embodiments of the second aspect, the coefficients are determined using regression analysis.

The applicant has appreciated that a suitably accurate characterisation of the oxygenator efficiency can be established by using regression analysis, such as non-linear regression. In embodiments, a Levenberg-Marquardt algorithm is used to determine the one or more coefficients.

In accordance with a third aspect of the invention, there is provided a blood gas analysis apparatus for determining the partial pressure of oxygen of arterial blood as defined by claim 15.

The apparatus is suitable for use with an oxygenator of the type configured to generate arterial blood by exposing venous blood to oxygen from an oxygenation gas and to allow passage of excess oxygenation gas as exhaust gas.

The apparatus comprises: one or more sensors configured to determine one or more gas values, wherein the gas values comprise a value suitable as an estimate of the partial pressure of oxygen in the exhaust gas, one or more sensors configured to determine one or more blood values, wherein the blood values comprise a blood oxygen uptake value, which is a value indicative of an amount of oxygen taken up by the blood in the oxygenator, and a controller. The controller is configured to receive as an input the one or more gas values and the one or more blood values, to calculate the partial pressure of oxygen in the arterial blood from the input by adjusting the estimate using the blood oxygen uptake value, and to generate an output of the partial pressure of oxygen in the arterial blood.

Embodiments of the third aspect are defined in the claims dependent on claim 14.

In embodiments of the third aspect, the sensors are capable of measuring one or more blood values comprising a venous oxygen saturation of the blood entering the oxygenator and an arterial oxygen saturation of the blood leaving the oxygenator. In such embodiments, the blood oxygen uptake can be calculated as the difference between the arterial oxygen saturation and the venous oxygen saturation.

In embodiments of the third aspect, the sensors are capable of measuring one or more gas values comprising one or more of the flow rate of the oxygenation gas, the amount or fraction of oxygen in the oxygenation gas, the amount or fraction of carbon dioxide in the oxygenation gas, the amount or fraction of carbon dioxide in the exhaust gas, and/or the partial pressure of oxygen in the exhaust gas.

In embodiments of the third aspect, the sensors are capable of measuring one or more blood values comprising the flow rate, the temperature, the pressure, and/or the haemoglobin concentration of the blood passing through the oxygenator.

In embodiments of the third aspect, the controller is configured to receive the total amount of exhaust gas as an input, to enable the controller to process an input based on an external parameter such as an exhaust gas flow parameter from a flow-control oxygenation system.

The controller may be configured to carry out any steps of the first or second aspect.

In embodiments of the third aspect, the apparatus is configured to receive as an input and store the one or more coefficients determined in accordance with the second aspect of the invention, and wherein the apparatus is configured to generate a coefficient-adjusted output of the partial oxygen pressure of the arterial blood as a function of the output and the one or more coefficients.

The controller may comprise a processor and software instructions implemented by the processor to carry out the steps defined in any embodiment of the first aspect and/or the second aspect.

BRIEF DESCRIPTION OF THE FIGURES

Exemplary embodiments of the invention will now be described with reference to the Figures, in which.

DETAILED DESCRIPTION

By way of background, an oxygenator is a device configured to receive oxygenation gas and venous blood, to re-oxygenate the blood by exposure to the oxygenation gas, and to provide oxygenated blood as arterial blood. Unused oxygenation gas is vented as exhaust gas which will also carry any gas given away by the blood.

Herein, the oxygenation gas is referred to as "inlet gas" with reference to the oxygenator. Note that in some literature the same oxygenation gas may be referred to differently (e.g. as "exit gas" with reference to a gas source). Herein, exit gas or exhaust gas denotes gas leaving the oxygenator.

Theory and Principle of Application

Determining $pO2$ Via Blood Oxygen Take-Up

Oxygenation gas (a mixture of gas components including oxygen) is supplied to an oxygenator at an inlet gas flow rate GI with an oxygen fraction fiO2 and a carbon dioxide fraction fiCO2.

In the oxygenator, oxygen O2 from the inlet gas is taken up by blood. The remaining gas leaves the oxygenator as exhaust gas through an exhaust port (an exhaust port in principle, as there are also ventilation ports, as explained below) at an exhaust gas flow rate GE. Knowledge of the fraction feO2 of oxygen GEO2 in the exhaust gas GE would be desirable because this is directly related to the partial pressure $pO2_{GE}$ of oxygen $O_2$ in the exhaust gas and the atmospheric (ambient) pressure Patm.

$$pO2_{GE} = feO2 \times Patm \qquad (1)$$

$$feO2 = GEO2/GE \qquad (2)$$

Equivalent considerations apply to the partial pressure $pCO2_{GE}$ of carbon dioxide CO2 in the exhaust gas GE.

$$pCO2_{GE} = feCO2 \times Patm \qquad (3)$$

$$feCO2 = GECO2/GE \qquad (4)$$

Flow rates GE, GEO2 and GECO2 may be referred to as "amounts" in day-to-day language, but are conventionally measured in L/min. The fractions feO2 and feCO2 are given as a percentage.

It follows that the partial pressure $pO2_{GE}$ may be calculated by determining the proportion of the amount GEO2 (of oxygen O2 in the exhaust gas GE) relative to relation to the exhaust gas GE.

However, the exhaust gas flow rate GE measured at the exhaust port of an oxygenator housing is not directly related to the total gas exiting the gas-blood interface (the gas-blood interface typically being provided in the form of hollow fibres) inside the oxygenator, because oxygenators are not air-tight. For safety reasons, an oxygenator housing comprises ventilation ports that prevent a pressure increase in the event of a blockage of the exhaust port. Such a pressure increase could lead, for example, to life-threatening gaseous blood emboli. Thus, the exhaust gas flow rate GE, if measured at the oxygenator exhaust port, may be affected by gas flow through ventilation ports and will not necessarily provide an accurate indication of the total exhaust gas given away from the gas-blood interface inside the oxygenator.

The present applicant has appreciated that it is possible to determine the fraction feO2 of oxygen O2 in the exhaust gas GE as the difference between (a) the oxygen supplied to the oxygenator as inlet gas oxygen GIO2 and (b) the oxygen taken up by the blood in the oxygenator. The oxygen take-up in the oxygenator can be described as the difference between the amount of oxygen in the arterial blood BEO2 (exiting the oxygenator in an oxygen-enriched state) and the venous blood BIO2 (entering into the oxygenator in an oxygen-decreased state).

Thus, the amount GEO2 of oxygen O2 in the exhaust gas GE is described by the difference between the amount of oxygen GIO2 supplied to the oxygenator and the amount of oxygen taken up by the blood (BEO2−BIO2).

$$GEO2 = GIO2 - (BEO2 - BIO2) \quad (5)$$

The values GIO2 and (BEO2−BIO2) are now considered in turn.

Oxygen Supply GIO2

The inlet gas flow rate GIO2 of oxygen O2 and the inlet gas flow rate GICO2 of carbon dioxide CO2 are a fraction fiO2 or fiCO2, respectively, of the total inlet gas flow rate GI.

The fraction fiO2 of oxygen and the fraction fiCO2 of carbon dioxide relative to the atmospheric pressure determine the partial pressure of oxygen or carbon dioxide, $pO2_{GI}$ and $pCO2_{GI}$, respectively.

$$GIO2 = GI \times fiO2 \quad (6)$$

$$fiO2 = pO2_{GI}/Patm \quad (7)$$

$$GICO2 = GI \times fiCO2 \quad (8)$$

$$fiCO2 = pCO2_{GI}/Patm \quad (9)$$

The factors at the right-hand side of equations 6 to 9 may be measured as follows: GI may be measured by a pressure drop technique (the higher the flow, the higher the pressure drop). To provide an illustrative example, the inlet gas flow rate may be measured using a mass flow meter or any other suitable method, e.g., a Venturi tube or an orifice plate. The units of the flow rate are usually L/min (1 min=60 seconds), but it is understood that other units may be used.

The partial pressure $pCO2_{GI}$ of carbon dioxide in the inlet gas may be measured with an optical (non-contact) sensor that provides an output indicative of the partial pressure $pCO2_{GI}$ of carbon dioxide CO2 in the inlet gas. fiCO2 is calculated according to equation 9. fiCO2 is dimensionless and typically given as a percentage.

The partial pressure $pO2_{GI}$ of oxygen in the inlet gas may be measured with a galvanic cell type oxygen sensor. A galvanic cell type oxygen sensor produces a voltage which is proportional to the partial pressure of oxygen in the inlet gas, and so is proportional to both the oxygen concentration and the gas pressure. The oxygen sensor may be calibrated with calibration gases having a known O2 fraction. For instance, readings may be obtained for two calibration gases, each having an externally verified oxygen content. A first calibration gas may have an oxygen fraction of 21% (v/v, in air). A second calibration gas may have 100% oxygen (i.e., for practical purposes pure oxygen). The oxygen sensor may take a first O2 sensor reading of the first calibration gas. The oxygen sensor may take a second O2 sensor reading of the second calibration gas. The ambient gas pressure Patm may also be measured so that it may be taken into account when calibrating the sensor. In operation, the sensor reading is thus relatable to values of known oxygen content values, and also the ambient gas pressure can be taken into account. fiO2 is a percentage value.

Patm may be obtained, for instance, via a direct measurement from an integrated sensor, and/or provided as an input parameter. For instance, Patm may be measured at the inlet or at the outlet of an oxygenator. A typical Patm value is in the region of 1013 mbar (1 atm).

The sensors for measuring the total inlet gas flow GI, the inlet gas oxygen fraction fiO2, and the inlet gas carbon dioxide fraction fiCO2 may be provided in a sensor unit. The sensors may be integrated into a single sensor unit. Conveniently, the sensor unit may be installed at the oxygenation gas inlet into the oxygenator. Exemplary measurement systems that are suitable for this purpose include the Spectrum System M™ range of diagnostic monitors available from Spectrum Medical Ltd, of Gloucester, GL2 9QL, England (the applicant of the present specification). The sensor unit may also comprise a sensor for measuring atmospheric pressure Patm.

Blood Oxygen Uptake (BEO2−BIO2)

In conditions where the supply GIO2 of oxygen into the oxygenator is relatively low, e.g. due to a low fiO2 fraction and/or a low inlet gas flow rate GI (known as "sweep"), the use of oxygen by a patient may be large enough to significantly lower the oxygen content of the gas. Therefore, in order to ensure that the algorithm for estimating GEO2 is applicable to a wide range of clinical scenarios, including scenarios with low oxygen supply, it is necessary to account for oxygen consumption by the patient, by way of the term BEO2−BIO2.

In the oxygenator, the exchange of oxygen O2 between the oxygenation gas and the blood depends on the partial oxygen pressures pO2, namely the partial oxygen pressure in the oxygenation gas, and the partial pressure $pO2_{BLOOD}$ in the blood: a higher gas partial oxygen pressure causes more oxygen to dissolve in blood and increases the blood partial oxygen pressure. In the absence of other influences the partial pressures will over time reach equilibrium. A notable property of blood is that oxygen will be bound by haemoglobin. The relationship between haemoglobin-bound oxygen and the blood partial oxygen pressure is complex, and the oxygen-binding properties of haemoglobin are dependent on various factors, such as temperature, pressure, blood pH, etc., which are omitted in this explanation for simplicity. As a simplification, it can be assumed that once bound to haemoglobin, an oxygen molecule no longer contributes directly to the blood partial oxygen pressure. Thus, the total amount of oxygen in blood includes oxygen dissolved in blood plasma, which determines the blood partial oxygen pressure $pO2_{BLOOD}$, and oxygen bound to haemoglobin, which does not contribute to $pO2_{BLOOD}$. Haemoglobin binds oxygen highly effectively and at physiological haemoglobin concentrations the amount of haemoglobin-bound oxygen exceeds the plasma-dissolved oxygen significantly.

For the determination of arterial blood BEO2 and venous blood BIO2 it can be assumed that the oxygen taken away from the inlet gas by dissolving directly in the blood plasma is negligible compared to that bound to haemoglobin. The present applicant has appreciated that, as a simplification, it can be assumed that oxygen in the inlet gas decreases only by binding to haemoglobin. Likewise, it can be assumed that an increase in haemoglobin-bound blood oxygen inside the oxygenator corresponds to the consumption of inlet gas oxygen.

The amount of oxygen bound to haemoglobin in a given volume of blood depends on the number of oxygen binding sites and, thus, the number of haemoglobin molecules per volume of blood and the level of oxygen saturation of the oxygen binding sites.

Thus, the amount BIO2 of oxygen O2 in the venous blood BI and the amount BEO2 of oxygen O2 in the arterial blood BE can be expressed as:

$$BIO2 = Hb \times 0.1551 \times Q \times 4 \times SvO2/100 \quad (10)$$

$$BEO2 = Hb \times 0.1551 \times Q \times 4 \times SaO2/100 \quad (11)$$

The values of the blood flow Q, the arterial oxygen saturation SaO2, the venous oxygen saturation SvO2, and the haemoglobin concentration Hb, can be obtained by non-contact measurement (examples described below). Conventionally, BIO2, BEO2, and Q are provided in L/min (1 min=60 seconds), Hb in g/dl (1 dl=0.1 L), and SaO2 and SvO2 percent. As an aside, one mol of haemoglobin weighs 64,458 g. It follows that 1 g of haemoglobin comprises 0.01551 mol, and a factor of 0.1551 allows g/dl to be converted to mmol/L. In equations 10 and 11, the factor 4 accounts for the number of oxygen molecules that can bind to each molecule of haemoglobin.

Blood flow Q may be measured by any suitable means, e.g., a Doppler flow meter or by determining the positive displacement of a peristaltic roller pump. The unit of the flow rate Q is usually L/min.

Oxygen saturation SO2 (both arterial oxygen saturation SaO2 and venous oxygen saturation SvO2) and haemoglobin concentration Hb may be measured by a non-contact optical measurement method locatable at a suitable position of the oxygenator. Exemplary optical measurements use LEDs and multiple-wavelength light sensors to determine blood absorption characteristics (the redness of blood changes depending on the haemoglobin oxygenation state). The unit of saturation is dimensionless and typically given percent. The haemoglobin concentration is conventionally provided in g/dl.

An exemplary measurement system that is capable of measuring the flow rate Q, haemoglobin concentration Hb, and both the arterial and venous oxygen saturation is the Spectrum System M™ range of diagnostic monitors available from Spectrum Medical Ltd, of Gloucester, GL2 9QL, England (the applicant of the present specification).

It is possible to determine BIO2 and BEO2 without contacting the blood via equations 10 and 11 when non-contact sensors are used to measure Q, Hb, SaO2 and SvO2. This is an advantage over using a contact electrode such as a Clark-type electrode. Even if, e.g., a conventional Clark-type electrode were to be used as a reference sensor for calibration prior to use, this avoids having to bring a blood sensor in direct blood contact during continual measurements of the quantities Q, Hb, SaO2 and SvO2. Of course, equations 10 and 11 are not limited to non-contact sensors; any suitable sensor may be used to measure these quantities.

It can further be assumed that during a relevant time scale the amount of haemoglobin in the venous blood (entering the oxygenator) and in the arterial blood (leaving the oxygenator) remains steady, as does the blood flow rate Q. Therefore, the blood oxygen uptake (BEO2–BIO2) can be described by equation 12:

$$(BEO2 - BIO2) = Hb \times 0.1551 \times Q \times 4 \times (SaO2 - SvO2)/100 \quad (12)$$

This allows the values BEO2 and BIO2 to be determined using a sensor for the blood flow Q and/or or the haemoglobin concentration Hb at a single location. For the avoidance of doubt, two sensors are used for the oxygen saturation measurements, one for arterial oxygen saturation SaO2 and one for venous oxygen saturation SvO2.

Relating the Amount GEO2 of Oxygen in the Exhaust Gas to the Fraction feO2

Via equation 5, the amount GEO2 of oxygen O2 in the exhaust gas GE can be determined without an exhaust gas sensor. Knowledge of the exhaust gas flow GE is then required to solve equations 2 and 4.

Direct Determination of Exhaust Gas Flow GE

Later in the present specification a description will follow of a non-conventional perfusion system design that allows the flow rate GE out of a main exhaust port of the oxygenator to be controlled. This provides a route to determining GE from the control parameters of the perfusion system.

Indirect Determination of Exhaust Gas Flow GE

However, with conventional oxygenators it is not possible to control the exhaust gas flow rate. As described above, because oxygenators are not closed systems, the exhaust gas flow GE measured at a conventional oxygenator exhaust port does not provide an accurate indication of the amount of exhaust gas exiting the gas-blood interface inside the oxygenator. An alternative to directly determining the exhaust flow rate GE is presented in the following passages of the present description.

The exhaust gas GE transported away from the oxygenator is assumed to consist of O2, CO2, and N2. Any amount of water H2O is assumed to be negligible. Likewise, any amount of substantially insoluble gases, such as noble gases and common fluorinated anaesthetic agents, is assumed to be either negligible or as included with the nitrogen term N2 for the purposes of pO2 prediction.

$$GE = GEO2 + GECO2 + GEN2 \quad (13)$$

GEO2 is determined via equation 5.

GECO2: According to equation 4, the amount GECO2 of carbon dioxide in the exhaust gas depends on the fraction feCO2 of carbon dioxide and the amount of exhaust gas GE. However, as will be shown in equations 17 to 19 below, a direct measurement of the fraction feCO2 of the carbon dioxide CO2 in the total exhaust gas flow GE will suffice for the purpose of determining an estimate of GE. The feCO2 sensor may be a stand-alone sensor at the exhaust port of the oxygenator.

GEN2: It is assumed that the amount of N2, and of any inert or largely insoluble gas, remains constant during oxygenation, i.e., that N2 is neither taken up nor given away by the blood.

$$GEN2 = GIN2 \quad (14)$$

For a determination of GIN2, it is assumed that the gas mixture GI consists only of O2, CO2, and N2, whereas the amount of water H2O and the amount of noble gases can be regarded as negligible and/or as included with the GIN2 term.

$$GI = GIO2 + GICO2 + GIN2 \quad (15)$$

By substituting right-hand terms of equation 15 with equations 6 and 8, the flow rate GIN2 of nitrogen N2 can be expressed as:

$$GIN2 = GI \times [1-(fiO2+fiCO2)] \quad (16)$$

The right-hand terms of equation 16, GI, fiO2, and fiCO2, can be measured by sensors at the oxygenator inlet as described above, avoiding a need for a separate measurement of the amount GIN2 of nitrogen N2 in the inlet gas GI or of the amount GEN2 in the outlet gas GE.

Thus, a sufficiently representative estimate of the outlet gas flow GE can be determined by substituting right-hand terms of equation 13 using equation 5 (for GEO2), equation 4 (for GECO2), and equations 14 and 16 (for GEN2).

$$GE = GEO2 + GIN2 + (feCO2 \times GE) \quad (17)$$

Thus, $GE - (feCO2 \times GE) = (GEO2 + GIN2)$ (18)

Thus, $GE = (GEO2 + GIN2)/(1 - feCO2)$ (19)

The fraction feCO2 of carbon dioxide in the exhaust gas can be assumed to be accurately determined by a direct sensor measurement from the main oxygenator exhaust port.

Having determined an estimate of GE via equation 19, the partial pressure $pO2_{GE}$ of oxygen in the exhaust gas can be obtained via equations 1 and 2.

Further increasing the accuracy of $pO2_{GE}$ By way of background, the inlet flow rates in L/min can be converted into mmol/min by assuming ideal gas conditions and that, therefore, 1 mol of gas occupies 22.41 L at standard temperature and pressure (STAP). The system may be configured to adjust for measured gas pressure. In practice, sufficient accuracy can be achieved by assuming that the ambient air has a temperature of 20° C. Alternatively, the ambient temperature may be measured by a sensor, allowing the temperature to be considered when converting L/min to mmol/min.

Blood temperature affects the partial pressure $pO2_{BLOOD}$ of blood oxygen. It was found by the applicant that it is possible to account for temperature effects by applying a linear offset, temperature term $offset_{TEMP}$, that correlates with blood temperature $T_{BLOOD}$ $$offset_{TEMP} = 2 \times (37 - T_{BLOOD}) \quad (20)$$

The blood temperature $T_{BLOOD}$ is the temperature of the blood entering or exiting the oxygenator in celsius. The blood temperature may be measured by any suitable thermometer. The thermometer may be located at a suitable location.

When calculating the oxygen uptake BEO2–BIO2 in the afore-described manner, simplifying assumptions are made about the oxygenator efficiency. The simplifying assumptions ignore that oxygen saturation is influenced by factors including the exchange area available for oxygenation, the blood flow rate (the slower the flow rate, the more time to approach equilibrium), and the oxygen load of the venous blood versus the desired oxygenation of the arterial blood (the bigger the difference, the more oxygen needs to cross an oxygenator membrane). This results in a non-linear influence of the blood flow rate Q and the difference in saturation (arterial oxygen saturation level SaO2–venous oxygen saturation level SvO2). The influence depends on the oxygenator type and can be described by an oxygenator term $offset_{OXYGENATOR}$:

$$offset_{OXYGENATOR} = A \times Q + B \times (SaO2 - SvO2) + C \times (Q \times (SaO2 - SvO2)) \quad (21)$$

As the oxygenator term $offset_{OXYGENATOR}$ comprises a term defining the blood oxygen uptake (SaO2–SvO2), the oxygenator term constitutes a blood oxygen uptake value indicative of an amount of oxygen taken up by the blood in the oxygenator.

The coefficients A, B and C in equation 21 are determined by best fitting of test values with experimental data obtained for a given oxygenator type. To provide an illustrative example, the coefficients for equation 18 for commercially available Medtronic Fusion and Terumo RX25 oxygenators, may be in the region of $$A = -4.1192379 \quad (22)$$

$$B = 1.4807944 \quad (23)$$

$$C = -1.5330679 \quad (24)$$

The coefficients depend on the oxygenator type and on the surface area and/or efficiency of the oxygenator membrane. In practice, the coefficients are obtained for a given oxygenator model by establishing the difference between $pO2_{BLOOD}$ as calculated and $pO2_{BLOOD}$ as measured by a reference method, e.g., using a conventional blood gas analyser. The difference is established in for a plurality of blood samples each oxygenated under different conditions. The oxygenation conditions may differ by the blood flow rate, temperature, inlet gas flow rate, inlet gas oxygen concentration, and/or venous blood oxygenation saturation. The number of blood samples is chosen to cover a wide range of values for each condition, including values that would be expected during typical use of an oxygenator and values that would not be expected in a clinical setting. Using an appropriate method, the coefficients A, B, and C are then adjusted so that the difference between the reference values (blood gas analyser values) and the calculated value for $pO2_{BLOOD}$ is minimised. For instance, the exemplary coefficients A, B, C of equations 22 to 24 have been determined on the basis of values measured from 40 samples from which a descriptive model was prepared using a least squares fitting method (using a Levenberg-Marquardt algorithm). Equation 21 is provided for illustrative purposes, and other fitting methods may be used. For instance, while the present example uses three coefficients A, B and C, a different number of coefficients may be appropriate depending on which mathematical model is used to describe the oxygenator term $offset_{OXYGENATOR}$. The coefficients can be determined off-line, during manufacture or setup. This allows the mathematical model to be optimised for a specific oxygenator, if required. The coefficients may be adjusted in the form of a retro-fit to existing equipment, e.g., as a software update. It is contemplated that the coefficients can be entered on a setup page. The setup page may be accessible to authorised personnel only.

A more accurate estimate $pO2_{EST}$ of the partial oxygen pressure is obtained by applying the temperature term $offset_{TEMP}$ and/or the oxygenator term $offset_{OXYGENATOR}$ to the partial pressure $pO2_{GE}$ as determined via equation 1.

$$pO2_{EST} = pO2_{GE} + offset_{TEMP} + Offset_{OXYGENATOR} \quad (25)$$

Thus, a more accurate estimate $pO2_{EST}$ can be understood as an output of the partial pressure of oxygen in the arterial blood, i.e., an output of the present invention, which is generated by way of equation 25 on the basis of an estimate of the partial pressure of oxygen in the exhaust gas (the estimate being constituted by $pO2_{GE}$) and on the basis of a blood oxygen uptake value (the blood oxygen uptake value being constituted by the term $offset_{OXYGENATOR}$ which is indicative of the amount of oxygen taken up in the oxygenator).

In use, various parameters of the clinical setting may cause an operational offset between the estimate $pO2_{EST}$ and the actual partial pressure $pO2_{BLOOD}$ of arterial blood leaving the oxygenator. The operational offset may be taken into account by a calibration or synchronisation step in order to further improve the accuracy of the estimate.

The synchronisation involves measuring the partial pressure $pO2_{BGA}$ using a blood gas analyser and comparing the value to the estimate $pO2_{EST}$ to calculate a synchronisation offset $offset_{SYNC}$.

$$offset_{SYNC} = pO2_{BGA} - pO2_{EST} \quad (26)$$

During ventilation procedures, blood samples are routinely obtained from a patient and their blood parameters are measured, usually with a blood gas analyser that measures several blood analytes including pO2 or pCO2. It is not untypical during a ventilation procedure for two, three, or more blood samples to be taken from the patient and analysed externally (e.g., in a blood gas analyser).

The time when a blood sample is taken for routine analysis may be registered as a sampling event, to register the sample with the estimated partial pressure $pO2_{EST}$ as estimated during the sampling event. Once the values from the blood analysis are available (which may take a few minutes), these can be related to the estimated values. For instance, a processor may be configured to correlate the blood analysis values $pO2_{BGA}$ with the value for $pO2_{EST}$ as determined at the time of the sampling event, to obtain a synchronisation offset via equation 26. The synchronisation offset can be applied to all future values to provide a more accurate reading. It would also be possible to apply the synchronisation offset retrospectively, i.e., to values of $pO2_{EST}$ determined and recorded at previous points in time.

To elaborate on equation 26, the synchronisation offset $offset_{SYNC}^{SAMPLE}$ is determined from a sample value $pO2_{BGA}^{SAMPLE}$ for a partial pressure estimate calculated during the sampling event $pO2_{EST}^{SAMPLE}$:

$$offset_{SYNC}^{SAMPLE} = pO2_{BGA}^{SAMPLE} - pO2_{EST}^{SAMPLE} \quad (27)$$

Subsequent blood partial oxygen pressure values $pO2_{BLOOD}^{CURRENT}$ are then calculated by applying the offset determined via equation 27 to the subsequent pO2 estimates $pO2_{EST}^{CURRENT}$.

$$pO2_{BLOOD}^{CURRENT} = pO2_{EST}^{CURRENT} + offset_{SYNC}^{SAMPLE} \quad (28)$$

Even though, in order to obtain the synchronisation value, a routine blood gas analysis or equivalent analysis may have to be performed, the blood partial oxygen pressure estimate obtained via equation 28 can be carried out more often than a blood sample analysis, i.e. results can be provided continuously or in defined intervals, e.g., every second.

Whenever a new blood sample is taken for a blood gas analysis, the synchronisation may be repeated. I.e., that sampling event may be registered in order to update via equation 27 the synchronisation offset value $offset_{SYNC}^{SAMPLE}$ that is then applied subsequently via equation 28.

Determining pO2 by Direct Measurement

As an alternative to determining $pO2_{BLOOD}$ via equation 5 using the algorithms set out above, the applicant discovered that the blood partial oxygen pressure $pO2_{BLOOD}$ may be related to the exhaust gas partial oxygen pressure $pO2_{GE}$ directly.

Measuring $pO2_{GE}$ directly requires no knowledge of the inlet gas properties (GI, fiO2, fiCO2) or of other (non-O2) exhaust gas properties (such as feCO2). However, if measured directly, $pO2_{GE}$ is affected by the amount of gas passing through any ventilation ports or auxiliary ports of the oxygenator and, thus, cannot be assumed to directly relate to the unconsumed oxygen in the inlet gas at the point it exits the gas-blood interface inside the oxygenator. As an aside, commercial pO2 sensors may provide the value of $pO2_{GE}$ as a percentage, based on the assumption that the reading is taken with reference to unity atmospheric pressure (1 atm=1013 mbar).

Using a sensor system capable of measuring blood temperature $T_{BLOOD}$, blood flow Q, and arterial and venous blood saturation SaO2 and SvO2, adjustment terms equivalent to equations 20 and 21 above can be calculated, to provide an estimated partial pressure $pO2_{EST}$ for the blood partial oxygen pressure.

$$offset_{TEMP} = 2 \times (37 - T_{BLOOD}) \quad (29)$$

$$offset_{OXYGENATOR} = A \times Q + B \times (SaO2 - SvO2) + C \times (Q \times (SaO2 - SvO2)) \quad (30)$$

$$pO2_{EST} = pO2_{GE} + offset_{TEMP} + offset_{OXYGENATOR} \quad (31)$$

Coefficients A, B, and C are determinable as set forth above. In particular, as the oxygenator term $offset_{OXYGENATOR}$ comprises a term defining the blood oxygen uptake (SaO2–SvO2), the oxygenator term constitutes a blood oxygen uptake value indicative of an amount of oxygen taken up by the blood in the oxygenator. Likewise, $pO2_{EST}$ can be understood as an output of the partial pressure of oxygen in the arterial blood, i.e., a output of the present invention, which is generated by way of equation 31 on the basis of an estimate of the partial pressure of oxygen in the exhaust gas (the estimate being constituted by $pO2_{GE}$) and on the basis of a blood oxygen uptake value (the blood oxygen uptake value being constituted by the term $offset_{OXYGENATOR}$ which is indicative of the amount of oxygen taken up in the oxygenator).

An aspect of the present invention includes a sensor system that is configured to continuously determine an estimate of the partial pressure $pO2_{GE}$ of oxygen in the exhaust gas, either by way of a measuring the input values required for equations 1-19 and a processor configured to process equations 1-19, or by direct measurement of the partial oxygen pressure $pO2_{GE}$ in the exhaust gas. In practice, the system may record values in defined intervals, e.g. every second.

The system may be configured to apply a temperature term $offset_{TEMP}$ and/or the oxygenator term $offset_{OXYGENATOR}$ to calculate an estimated partial pressure $pO2_{EST}$ in accordance with equation 25 or 31.

For synchronisation, the sensor system may be configured to register a sampling event. A sampling event occurs when a blood sample is taken, and pO2 estimates determined at the time of the blood sampling can be associated with the blood sample. In a clinical setting, it may take a few minutes until blood sample values are available. During this time, the sensor system is able to continue determining pO2 estimates. Once the values from the blood analysis are available, these can be entered into the sensor system. The sensor system is configured to correlate the blood analysis values with the pO2 estimates determined during the sampling event. This allows any deviation between the blood value and the estimate to be determined, and a synchronisation value can be applied to the sensor values. It is then possible to apply the synchronisation value to future pO2 estimates determined by the sensor system.

In this manner, a large number of readings can be made, whereas it would not be practical to take and analyse a large number of blood samples. The pO2 estimates can be determined continuously or in defined intervals.

Multiple sampling events may be registered, whenever appropriate, e.g. according to the number of blood samples taken during an intervention, in order to update the synchronisation offset.

By applying a synchronisation offset, a more accurate determination of the arterial partial oxygen pressure $pO2_{BLOOD}$ to be made based on the estimate derived from the partial oxygen pressure $pO2_{GE}$, which can be obtained without blood contact.

Temperature Considerations

Because the reading of many blood analytes is dependent on temperature, the blood gas values of pO2 and pCO2 are typically obtained at a standardised temperature. Most blood gas analysers set the blood sample temperature to 37° C. as the standardised temperature.

However, also the partial pressures pO2 and pCO2 are temperature-dependent. It is often the case that the blood circulating in the oxygenator has a different temperature than the temperature-controlled sample in the blood gas analyser. For instance, the body temperature and blood of a patient may be cooled to significantly below 37° C. during surgery, whereas a blood gas analyser may routinely warm the blood to 37° C. In contrast, any values obtained by sensors from the oxygenator will be close to the patient temperature. Any difference between the blood temperatures needs to be taken into account.

A suitable temperature adjustment to obtain a temperature-adjusted value $pO2_{ADJ}$ or $pCO2_{ADJ}$, respectively, may be obtained using known equations.

$$pO2_{ADJ} = pO2_{BLOOD} 10^{\left(\frac{0.0252}{0.234\left(\frac{pO2_{BLOOD}}{100}\right)^{3.88} + 1} + 0.00564\right)*(t-37)} \quad (32)$$

$$pCO2_{ADJ} = pCO2_{BLOOD} 10^{(0.019)*(t-37)} \quad (33)$$

Equation 32 corresponds to the formula used by the Radiometer AML-3, and equation 33 corresponds to the formula used by Corning Models 178, 170, 168 and 158, both reported by Edward R. Ashwood in Clinical Chemistry Vol 29 No 11, pg 1877 (1993).

Exemplary Procedure

Figure 1:
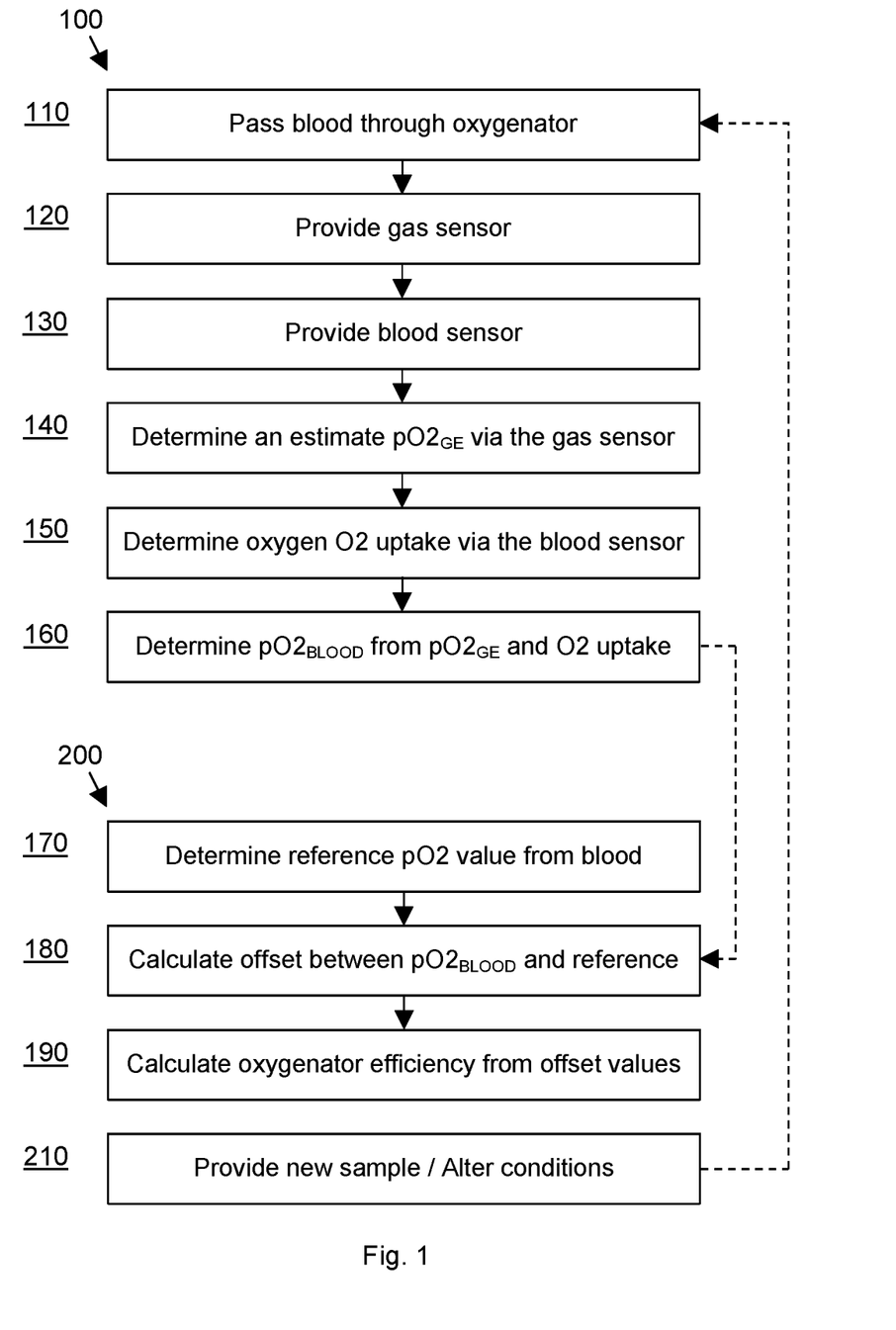
FIG. 1 shows steps of an exemplary sequence of method steps in accordance with embodiments of the invention.

Turning to FIG. 1, a sequence of steps of a method 100 in accordance with the above principles are shown. In step 110, blood is provided for oxygenation through an oxygenator. In step 120, a sensor system is provided suitable for determining one or more gas values. In step 130, a sensor system is provided suitable for determining one or more blood values. In step 140, one or more gas values are determined, the gas values comprising an estimate of the partial pressure of oxygen in the exhaust gas of the oxygenator. In step 150, one or more blood values are determined, the blood values comprising a blood oxygen uptake value indicative of an amount of oxygen taken up by the blood in the oxygenator. In step 160, an output is generated by using the blood oxygen uptake value to adjust the estimate of the partial pressure of oxygen in the exhaust gas.

Some or all steps of method 100 may be carried out to implement one or more of the algorithms described above.

Step 150 may comprise measuring the venous oxygen saturation of the blood entering the oxygenator, measuring the arterial oxygen saturation of the blood leaving the oxygenator, and calculating the blood oxygen uptake value as a function of the difference between the arterial oxygen saturation and the venous oxygen saturation.

Step 150 may comprise measuring the flow rate, the temperature, and/or the haemoglobin concentration of the blood passing through the oxygenator. Step 150 may comprise calculating the blood oxygen uptake value as a function of the flow rate, the temperature, and/or the haemoglobin concentration. Step 160 may comprise calculating the output as a function of the flow rate, the temperature, and/or the haemoglobin concentration.

Step 140 may comprise obtaining a measurement of the partial pressure of oxygen in the exhaust gas and using the measurement as the estimate.

Step 140 may comprise determining the amount of oxygen in the exhaust gas and the amount of exhaust gas leaving the oxygenator, determining the fraction of oxygen in the exhaust gas as a quotient of the amount of oxygen in the exhaust gas and the amount of exhaust gas, and deriving the estimate of the partial pressure of oxygen in the exhaust gas from the fraction of oxygen in the exhaust gas.

Step 140 may further comprise determining an inlet gas value indicative of the amount of oxygen entering the oxygenator. Step 160 may comprise determining the amount of oxygen in the exhaust gas based on the difference between the inlet gas value and the blood oxygen uptake value.

Step 140 may comprise measuring one or more of the total amount of the oxygenation gas, the amount or fraction of oxygen in the oxygenation gas, the amount or fraction of carbon dioxide in the oxygenation gas, and the amount or fraction of carbon dioxide in the exhaust gas.

Included in FIG. 1 is a method 200 for characterising the oxygenation efficiency of an oxygenator. The method 200 employs the steps of method 100 for a plurality of blood samples.

In step 170, a reference value of the partial pressure of oxygen in the arterial blood is obtained using a reference method, such as by measuring the blood in a conventional blood gas analyser.

In step 180, an offset value is calculated to describe the difference between the output generated in step 160 and the reference value measured in step 170. The offset value may be used to adjust the output.

In step 190, one or more coefficients for a model describing the oxygenation efficiency of an oxygenator are calculated based on multiple offset values.

In step 210, a blood sample or blood volume is provided for oxygenation in the oxygenator, and one or more of the conditions for steps 110 to 160 are altered, before steps 110 to 160 are repeated.

Flow-Control Oxygenator

The algorithms above apply to oxygenators that are conventional in the sense that the amount/proportion of gas or ambient air passing through auxiliary/ventilation ports is treated as an unknown quantity, and so the amount of exhaust gas GE and any components therein are not directly relatable to the amount of exhaust gas exiting the gas-blood interface inside the oxygenator.

For the understanding of some embodiments, described herein is an unconventional oxygenation system that allows the flow rates of oxygenation gases into an oxygenator and/or of exhaust gases out of an oxygenator to be determined by control of gas flow parameters. Herein, such an unconventional oxygenation system may be referred to as a "flow-control" oxygenation system. The flow-control oxygenation system disclosed herein is described in the applicant's co-pending United Kingdom patent application number GB1421498.5.

Embodiments of the present invention may be incorporated in or make use of a flow-control oxygenation system. In that case, the flow rate of the exhaust gas GE out of the main oxygenator exhaust port may be considered in the determination of blood or oxygenation gas parameters. For instance, instead of determining GE by way of equation 19 above, it may be possible to derive an estimate of GE from flow control parameters.

In one operating mode, a flow-control oxygenation system may allow a flow rate to be applied that sucks only a fraction of the gas leaving the gas-blood interface. Any remaining amount of exhaust gas would leave the oxygenator via the ventilation ports. In that case, the composition of the fraction of the exhaust gas through the oxygenator exhaust port will closely correspond to the composition of the gas leaving the gas-blood interface inside the oxygenator, because it is not diluted by ambient air drawn in via the ventilation ports. This will allow a more accurate measurement to be made of the fraction of a component of the exhaust gas, such as the fraction feO2 of oxygen in the exhaust gas. This operating mode may be appropriate if there is no concern about unused oxygenation gas leaking out of the oxygenator, for instance during extracorporeal ventilation without anaesthesia.

In one operating mode, a flow-control oxygenation system may allow a flow rate high enough to suck all of the exhaust gas leaving the gas-blood interface inside the oxygenator, and also ambient air drawn into the oxygenator housing via ventilation ports. In that case, the composition of the exhaust gas through the oxygenator exhaust port includes ambient air. This operating mode may be appropriate if passage of unused oxygenation gas (e.g., comprising unused anaesthetic agent) out of the oxygenator is of concern. This operating mode may also be necessary to achieve sufficiently accurate measurements if the flow rate of oxygenation gas into the oxygenator is low. With knowledge of the composition of the ambient air and knowledge of the flow rate of the oxygenation gas entering the oxygenator, the oxygen concentration just after the gas-blood interface may be determined.

Values determined via the different operating modes, e.g. the fraction of an exhaust gas component or the amount of exhaust gas, may be used to solve the algorithms above.

In particular, the applicant contemplates that the various methods described herein may be used in a complementary fashion. For instance, in a flow-control oxygenator, the flow rate of the exhaust gas GE may be determined both via equation 19 above and via derivation from flow-control parameters.

Components Overview of a Flow-Control Oxygenation System

Figure 2:
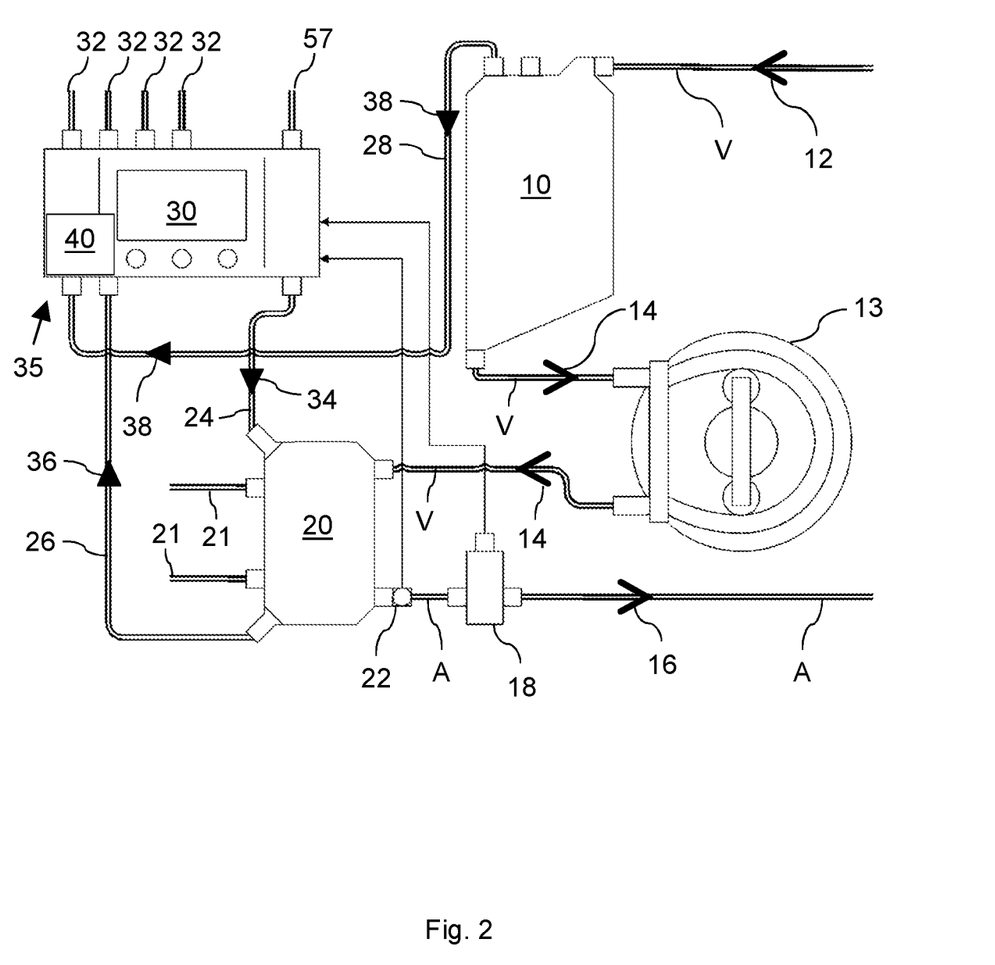
FIG. 2 shows a schematic layout of components of an exemplary ventilation system described herein for the understanding of an embodiment of the invention.

FIG. 2 provides an overview of system components of a flow-control ventilation system for use with embodiments of the present invention. By way of background, an oxygenator is a device configured to receive oxygenation gas and venous blood, to re-oxygenate the blood by exposure to the oxygenation gas, and to provide oxygenated blood as arterial blood. Unused oxygenation gas is vented as exhaust gas which will also carry any gas given away by the blood. Put simply, a pulmonary (blood) bypass loop crosses a gas (oxygen) line. The pulmonary bypass loop circulates blood from a patient in order for the blood to be oxygenated and to be returned to the patient. The gas line provides the oxygenation gas for blood oxygenation.

Pulmonary Bypass Loop (Blood)

Venous blood from a patient (not shown in FIG. 2) is circulated in the direction indicated by arrow 12 towards a reservoir 10 via a venous line V. From the reservoir 10, the venous blood is pumped by a pump 13 in the direction indicated by arrows 14 towards an oxygenator 20. In the oxygenator 20, the blood is oxygenated. Blood leaves the oxygenator 20 to be supplied, as arterial blood, via an arterial line A in the direction indicated by arrow 16 towards a patient. A flow sensor 18 is provided to measure the flow rate of the re-oxygenated blood exiting the oxygenator 20. A temperature sensor 22 is provided to measure the temperature of the re-oxygenated blood exiting the oxygenator 20. Water lines 21 connect the oxygenator 20 to a water bath for maintaining a predefined temperature.

Oxygenation Gas Line

A gas circulator 35 comprises a blender 30 for preparation of oxygenation gases. In the particular embodiment described herein, the blender also comprises a vacuum subsystem 40 for removal of exhaust gases. However, conventional oxygenation gas blending systems do not comprise a vacuum sub-system.

Gases, such as nitrogen (N2) and oxygen (O2) of predetermined purity levels are supplied from hospital supply lines 32 into a blender 30. Compressed air with a composition of about 79% nitrogen and 21% oxygen may be supplied. Hospital-supplied gases may contain traces of carbon-dioxide and/or noble gases. The hospital mains also provide a source of low pressure or vacuum. The hospital supplies may also include oxygenation gas of a predetermined composition or oxygen at a predetermined purity level, which may be supplied via a supply line 57 to the blender 30.

In the blender 30, the gases are mixed to a composition that is to be supplied to the oxygenator 20 and fed in the direction indicated by arrow 34 via a supply line 24. In the oxygenator 20, the haemoglobin molecules of the venous blood are to take up oxygen and to release carbon dioxide. In the oxygenator 20, other gases, such as waste anaesthetic gases, may be released from or not be taken up in the oxygenator. Any gases released in or passing through the oxygenator 20 and gas components not taken up from the inlet gas are collected as waste gas or exhaust gas and leave the oxygenator 20 via an exhaust line 26 in the direction of arrow 36 and are transported away. The gas flow via the exhaust line 26 is assisted by a vacuum. In the embodiment described herein, the vacuum is supplied via a vacuum subsystem 40 that is part of the gas circulator 35. Conventionally, an oxygenator is connected directly to a hospital vacuum port.

Components Operation

The operation of the oxygenator 20, the blender 30 and the vacuum sub-system 40 will now be described in more detail with reference to FIGS. 3, 4 and 5.

Oxygenator 20

Figure 3:
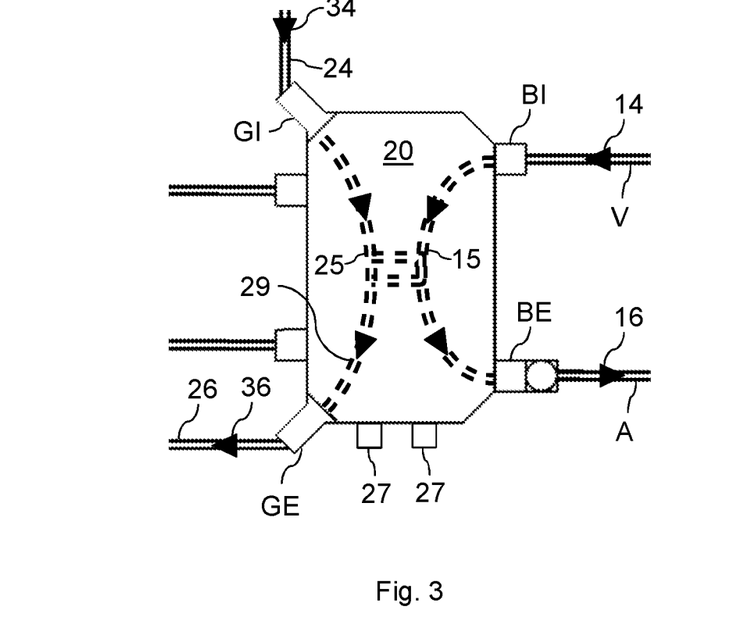
FIG. 3 shows an oxygenator of an exemplary ventilation system described herein for the understanding of an embodiment of the invention.
Figure 4:
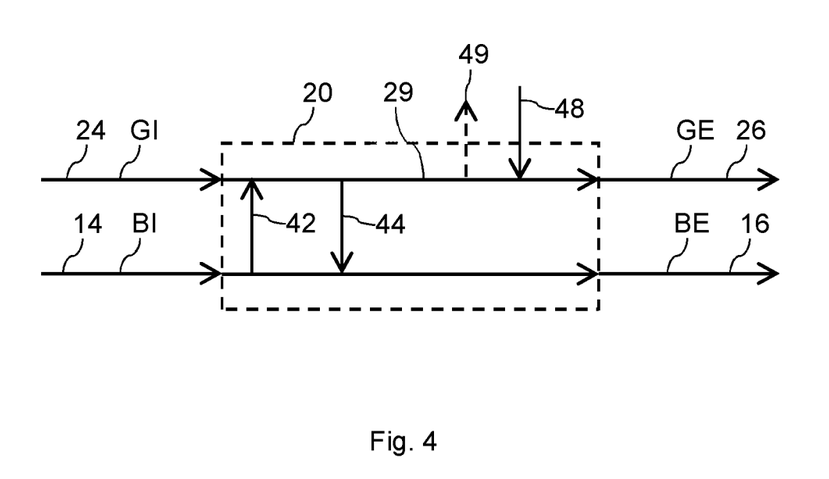
FIG. 4 shows a schematic flow analysis for the FIG. 3 oxygenator, described herein for the understanding of an embodiment of the invention.

Venous blood carrying CO2 enters the oxygenator 20 via venous line V (in direction 14), as shown in detail in FIGS. 3 and 4. Venous blood enters the oxygenator 20 in a condition indicated herein by the symbol BI. In particular, the blood transports an amount of oxygen BIO2 and an amount of carbon dioxide BICO2 per unit of time.

FIG. 3 illustrates the uptake of oxygen by the blood in the oxygenator 20. The venous blood is transported within the oxygenator 20 along line 15 and exposed to the gas mixture, inlet gas GI from the blender 30, that is transported along the line 25. The gas mixture GI has a higher oxygen partial pressure and a lower carbon dioxide partial pressure than the blood, causing the haemoglobin to release CO2 and take up O2.

Although FIG. 3 indicates, schematically, a concurrent exchange, oxygenators use, in practice, a countercurrent exchange.

FIG. 4 illustrates a flow diagram. In the oxygenator 20, CO2 is released from the blood into the gas stream, as indicated by arrow 42. The blood stream takes up 02 in a reaction indicated by arrow 44. Other components, such as waste anaesthetic gas, may not be taken up by the blood and enter or remain in the exhaust gas stream as indicated by arrow 46. Oxygenated blood is referred to as arterial blood.

The oxygenator 20 is not an air-tight unit. It may comprise one or more secondary (i.e., ventilation) exhaust ports 27 as a failsafe measure, to avoid pressure build-up within the oxygenator 20 if the exhaust line 26 is blocked. As the secondary exhaust ports 27 permit passage of air or gases, the amount of exhaust gas GE leaving the oxygenator 20 at the exhaust line 26 cannot be assumed to be identical to the amount of exhaust gas at a point 29 immediately downstream of the gas-blood interface inside the oxygenator 20.

As or if a vacuum-induced flow is applied via exhaust line 26, this draws, therefore, not only exhaust gas GE from the oxygenator 20, but also ambient air 48 via secondary exhaust ports 27. To provide an illustrative example, for every 2 L of gas mixture supplied into the oxygenator 20 via supply line 24, 2.1 L of exhaust gas may be drawn through exhaust line 26.

The difference in flow rates that causes ambient air 48 to be drawn into the oxygenator 20 can also be used to ensure that any waste anaesthetic gas 46 is removed via the exhaust line 26. Thus, waste anaesthetic gas 46 is prevented from seeping out of the oxygenator 20, as indicated by arrow 49, into the operating theatre, where anaesthetic gases could affect staff.

Arterial blood leaves the oxygenator 20 in a condition BE. The amount of oxygen of the arterial blood BEO2 is related to the arterial oxygen saturation SaO2 and also depends on the haemoglobin concentration in the blood.

Exhaust gas GE which carries components released from the blood, such as CO2 from transfer 42, or waste anaesthetic gas that has not been taken up inside the oxygenator 20, is drawn via exhaust line 26 towards the vacuum sub-system 40 of gas circulator 35.

Blender 30

Figure 5:
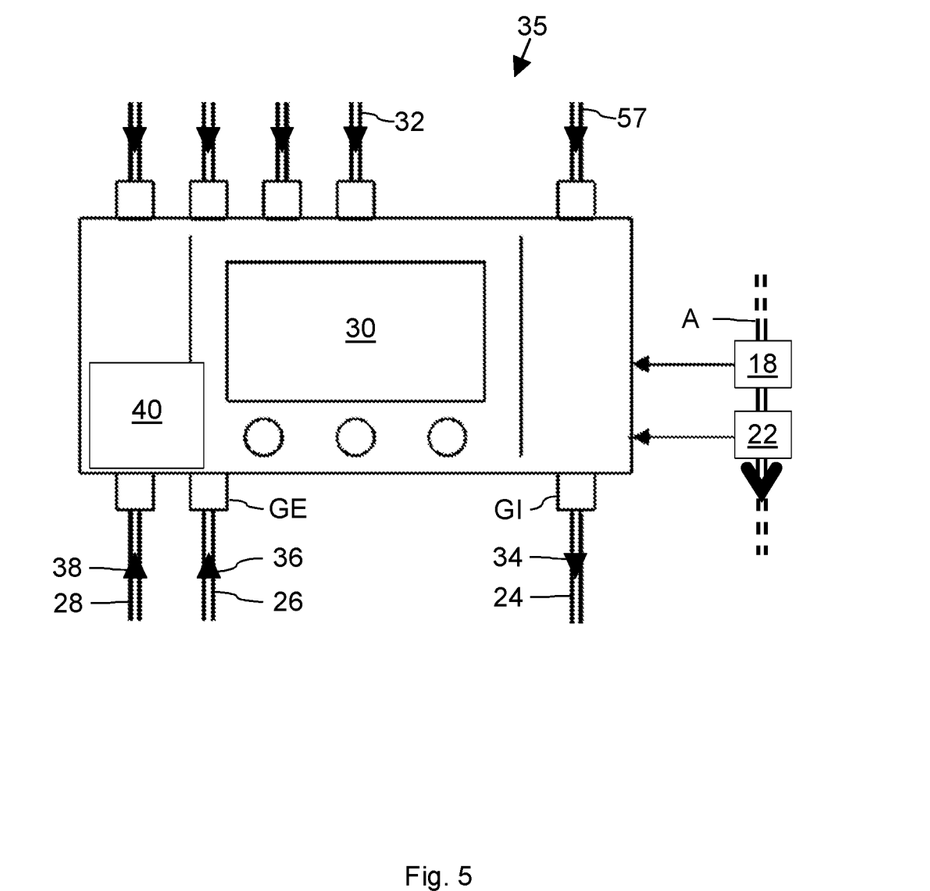
FIG. 5 shows a gas blender for use with a ventilation system, described herein for the understanding of an embodiment of the invention.

In FIG. 5, the blender 30 is drawn enlarged as part of the gas circulator 35. Gas components supplied via inlets 32 are mixed to provide a supply gas for the oxygenator 20. Hospital-supplied gases 32 are blended to an oxygenation gas of predetermined properties before this is supplied at a predetermined flow rate via supply line 24 to the oxygenator 20. The blender may comprise an anaesthesia supply, such as an anaesthesia vaporiser, for supplying anaesthetic agent into the oxygenation gas.

Vacuum Subsystem 40

Vacuum may be used to create a flow gradient to assist gas flow. In the system described herein, the vacuum pressure gradients are controlled by a vacuum subsystem 40 which in turn is supplied from a single vacuum supply, e.g. from a hospital.

The flow gradient in the exhaust line 26 is indicated by arrow 36 and pulls exhaust gas from the oxygenator 20.

To illustrate this with an example, supply gas GI may be supplied to the oxygenator 20 at a rate of 2 L/min. The vacuum sub-system may be set to withdraw exhaust gas at a flow rate of 2.1 L/min. Thus, it can be assumed that, absent any influences by the blood oxygenation processes, 0.1 L/min (0.1 L/min=2.1 L/min exhaust gas–2.0 L/min inlet gas) of ambient air were drawn in via the oxygenator.

The combination of the blender 30 and the vacuum sub-system 40 in a gas circulator 35 facilitates the integration of sensor and the evaluation of measured properties of the oxygenation gas and the exhaust gas (e.g., flow rate, pressure, temperature, composition, oxygen fraction, carbon dioxide fraction, and combinations thereof).

Although the gas supply 32 and 57 is described herein as being provided by a hospital, this is exemplary for a typical setting. The gas supply may be provided by another source. Any number and type of supply gases may be used, according to requirements.

The invention claimed is:

1. A blood gas analysis method for determining the partial pressure of oxygen of arterial blood exiting an oxygenator, the oxygenator being of a type configured to generate arterial blood by exposing venous blood to oxygen from an oxygenation gas and to allow passage of excess oxygenation gas as exhaust gas, the method comprising the steps of:
   determining at least one gas value, the at least one gas value being indicative of a property of the exhaust gas;
   determining at least one blood value, the at least one blood value comprising a blood oxygen uptake value indicative of an amount of oxygen taken up by the blood in the oxygenator;
   calculating an estimate of the partial pressure of oxygen in the exhaust gas as a function of the at least one gas value and the at least one blood value; and
   generating an output of the partial pressure of oxygen in the arterial blood based on the estimate of the partial pressure of oxygen in the exhaust gas and the blood oxygen uptake value.

2. The blood gas analysis method according to claim 1, wherein the blood oxygen uptake value is derived by
   determining an arterial oxygen saturation of the arterial blood;
   determining a venous oxygen saturation of the venous blood; and
   calculating the blood oxygen uptake value as a function of the difference between the arterial oxygen saturation and the venous oxygen saturation.

3. The blood gas analysis method according to claim 2, wherein at least one of the blood oxygen uptake value and the output of the partial pressure of oxygen in the arterial blood is calculated as a function dependent on at least one selected from the group consisting of: (a) a flow rate, (b) a temperature, and (c) a haemoglobin concentration of the blood passing through the oxygenator.

4. The blood gas analysis method according to claim 1, wherein calculating the estimate of the partial pressure of oxygen in the exhaust gas comprises the steps of:
   determining a plurality of gas values, the gas values comprising the amount of oxygen in the exhaust gas and the amount of exhaust gas leaving the oxygenator;
   determining the fraction of oxygen in the exhaust gas as a quotient of the amount of oxygen in the exhaust gas and the amount of exhaust gas; and deriving the estimate of the partial pressure of oxygen in the exhaust gas from the fraction of oxygen in the exhaust gas.

5. The blood gas analysis method according to claim 4, wherein calculating the amount of oxygen in the exhaust gas comprises the steps of:
   determining an inlet gas value indicative of the amount of oxygen entering the oxygenator;
   determining the blood oxygen uptake value as a function of a flow rate and a haemoglobin concentration of the blood passing through the oxygenator; and
   determining the amount of oxygen in the exhaust gas based on the difference between the inlet gas value and the blood oxygen uptake value.

6. The blood gas analysis method according to claim 4, wherein determining the amount of exhaust gas leaving the oxygenator comprises using a flow-control oxygenation system to set a flow rate of the exhaust gas and to derive an amount of exhaust gas from the flow rate parameters as controlled by the flow-control oxygenation system.

7. The blood gas analysis method according to 4, wherein the amount of exhaust gas leaving the oxygenator is calculated as a function of at least one gas value, the at least one gas value comprising at least one selected from the group consisting of: a total amount of the oxygenation gas, an amount of oxygen in the oxygenation gas, a fraction of oxygen in the oxygenation gas, an amount of carbon dioxide in the oxygenation gas, a fraction of carbon dioxide in the oxygenation gas, an amount of carbon dioxide in the exhaust gas, and a fraction of carbon dioxide in the exhaust gas.

8. The blood gas analysis method according to claim 4, wherein the amount of exhaust gas leaving the oxygenator is calculated as a function of at least one blood value, the at least one blood value comprising at least one selected from the group consisting of: a flow rate, a temperature, a pressure, a haemoglobin concentration, and an oxygen saturation, of at least one of the blood entering and exiting the oxygenator.

9. The blood gas analysis method according to claim 1, further comprising adjusting an oxygenation parameter in response to the output of the partial pressure of oxygen in the arterial blood.

10. The blood gas analysis method according to claim 1, the method used to characterize an oxygenation efficiency of an oxygenator, the method further comprising the steps of:
   providing at least one blood sample and oxygenating each blood sample in the oxygenator;
   determining the blood values for each sample;
   determining the gas values for each sample;
   determining for each sample as a sample-specific output the output of the partial pressure of oxygen in the arterial blood;
   determining for each sample a sample-specific reference value of the partial pressure of oxygen in the arterial blood;
   calculating, for each sample, an offset value indicating any difference between the sample-specific output and the sample-specific reference value; and
   generating at least one coefficient based on at least one offset value to describe the oxygenation efficiency of the oxygenator.

11. A blood gas analysis apparatus for determining the partial pressure of oxygen of arterial blood exiting an oxygenator, the oxygenator being of a type configured to generate arterial blood by exposing venous blood to oxygen from an oxygenation gas and to allow passage of excess oxygenation gas as exhaust gas, wherein the apparatus comprises:
   at least one sensor configured to determine at least one gas value;
   at least one sensor configured to determine at least one blood value, the at least one blood value comprising a blood oxygen uptake value, the blood oxygen uptake value being a value indicative of an amount of oxygen taken up by the blood in the oxygenator; and
   a controller configured
      to receive as an input the at least one gas value and the at least one blood value,
      to calculate an estimate of the partial pressure of oxygen in the exhaust gas as a function of the at least one gas value and the at least one blood value; and
      to generate an output of the partial pressure of oxygen in the arterial blood based on the estimate of the partial pressure of oxygen in the exhaust gas and the blood oxygen uptake value.

12. The apparatus according to claim 11, wherein the at least one blood value comprises a venous oxygen saturation of the blood entering the oxygenator and an arterial oxygen saturation of the blood leaving the oxygenator, and wherein the blood oxygen uptake is calculated as the difference between the arterial oxygen saturation and the venous oxygen saturation.

13. The apparatus according to claim 11, wherein the at least one gas value comprises at least one selected from the group consisting of: a flow rate of the oxygenation gas, an amount of oxygen in the oxygenation gas, a fraction of oxygen in the oxygenation gas, an amount of carbon dioxide in the oxygenation gas, a fraction of carbon dioxide in the oxygenation gas, an amount of carbon dioxide in the exhaust gas, and a fraction of carbon dioxide in the exhaust gas.

14. The apparatus according to claim 11, wherein the at least one blood value comprise at least one selected from the group consisting of: a flow rate, a temperature, a pressure, and a haemoglobin concentration of the blood passing through the oxygenator.

15. The apparatus according to claim 11, wherein the controller is configured to receive the total amount of exhaust gas as an input, to enable the controller to process an input based on an external parameter such as an exhaust gas flow parameter from a flow-control oxygenation system.

16. The apparatus according to claim 11, wherein the apparatus is configured to:
   receive, as an input, and store a coefficient, the coefficient based, at least in part, on at least one offset value indicating any difference between a sample-specific output and a sample-specific reference value, and
   generate a coefficient-adjusted output of the partial oxygen pressure of the arterial blood as a function of the output and the coefficient.

17. The apparatus according to claim 11, further configured to effect an adjustment of an oxygenation parameter based on the output of the partial pressure of oxygen in the arterial blood.

18. The apparatus according to claim 11, wherein the controller comprises a processor and software instructions implemented by the processor for:
   determining the at least one gas value;
   determining the at least one blood value;
   calculating the estimate of the partial pressure of oxygen in the exhaust gas as a function of the at least one gas value and the at least one blood value; and generating the output of the partial pressure of oxygen in the arterial blood based on the estimate of the partial pressure of oxygen in the exhaust gas and the blood oxygen uptake value.

\* \* \* \* \*